(12) United States Patent
Kleinert et al.

(10) Patent No.: US 8,402,830 B2
(45) Date of Patent: Mar. 26, 2013

(54) METHOD FOR THE NON-DESTRUCTIVE TESTING OF A TEST OBJECT BY WAY OF ULTRASOUND AND APPARATUS THEREFOR

(75) Inventors: Wolf-Dietrich Kleinert, Bonn (DE); York Oberdörfer, Köln (DE)

(73) Assignee: GE Sensing & Inspection Technologies GmbH (DE)

( * ) Notice: Subject to any disclaimer, the term of this patent is extended or adjusted under 35 U.S.C. 154(b) by 271 days.

(21) Appl. No.: 12/811,562

(22) PCT Filed: Dec. 8, 2008

(86) PCT No.: PCT/EP2008/067044
§ 371 (c)(1),
(2), (4) Date: Sep. 23, 2010

(87) PCT Pub. No.: WO2009/087004
PCT Pub. Date: Jul. 16, 2009

(65) Prior Publication Data
US 2011/0016978 A1    Jan. 27, 2011

(30) Foreign Application Priority Data

Jan. 4, 2008 (DE) .......................... 10 2008 003 257
Apr. 11, 2008 (DE) .......................... 10 2008 018 648
Aug. 7, 2008 (DE) .......................... 10 2008 037 173

(51) Int. Cl.
*G01N 29/24* (2006.01)
(52) U.S. Cl. ........................................... 73/629; 73/602
(58) Field of Classification Search .................... 73/629, 73/602, 622, 632
See application file for complete search history.

(56) References Cited

U.S. PATENT DOCUMENTS

| | | | | |
|---|---|---|---|---|
| 4,111,557 | A | * | 9/1978 | Rottenkolber et al. ........ 356/394 |
| 5,511,425 | A | | 4/1996 | Kleinert et al. |
| 6,993,972 | B2 | * | 2/2006 | Basir et al. ...................... 73/625 |
| 7,204,129 | B2 | * | 4/2007 | Basir et al. .................... 73/54.41 |
| 8,127,612 | B2 | | 3/2012 | Mitchell |
| 2006/0219013 | A1 | | 10/2006 | Baba |
| 2006/0241456 | A1 | | 10/2006 | Karasawa |

(Continued)

FOREIGN PATENT DOCUMENTS

| | | |
|---|---|---|
| DE | 2335567 A1 | 2/1975 |
| DE | 2901818 | 7/1980 |

(Continued)

OTHER PUBLICATIONS

International Search Report PCT/EP2008/067044; Dated May 20, 2009.

(Continued)

*Primary Examiner* — J M Saint Surin
(74) *Attorney, Agent, or Firm* — Cantor Colburn LLP

(57) ABSTRACT

A method for nondestructive testing of a test object by means of ultrasound, and a corresponding device, the method including
  radiating directed ultrasonic pulses into the test object 100 at an irradiation angle $\beta$, whereby the irradiation angle $\beta$ is set electronically,
  recording of echo signals that result from the ultrasonic pulses radiated into the test object 100,
  determining an ERS value of an error 102 in the volume of the test object from echo signals, which can be associated with the error 102.

24 Claims, 5 Drawing Sheets

U.S. PATENT DOCUMENTS

| | | | |
|---|---|---|---|
| 2011/0016978 A1 | 1/2011 | Kleinert et al. | |
| 2011/0016979 A1* | 1/2011 | Oberdorfer et al. | 73/632 |
| 2012/0024067 A1* | 2/2012 | Oberdoerfer et al. | 73/632 |
| 2012/0095346 A1* | 4/2012 | Yoshizawa et al. | 600/459 |
| 2012/0099397 A1* | 4/2012 | Inoue et al. | 367/87 |

FOREIGN PATENT DOCUMENTS

| | | |
|---|---|---|
| WO | 2007144271 | 12/2007 |

OTHER PUBLICATIONS

Deutsch V. et al.: "3.4 Fehlernachweis und Geratejustierung" Ultraschallpruefung: Grandlagen und Industrielle Anwendungen, XX, XX, Jan. 1, 1997, pp. 80-133, p. 107, XP002280036.

International Search Report, PCT/EP2009/054102; dat of Mailing Oct. 5, 2009, European Patent Office.

International Search Report; International Application No. PCT/EP2008/068236; dated May 25, 2009.

Bohn H, et al. "Apparative Development for in-service Inspection of reacotr pressure vessels" Nuclear Engineering and Design, Amsterdam, NL, vol. 102, No. 3, Jan. 1, 1987, pp. 341-355, XP002448121, ISSN: 0029-5493.

Deutsch V, et al. "3.4 Fehlemachweis und Geratejustierung" Ultraschallpreufung: Grundlagen Und Industielle Anwendungeon, Jan. 1, 1997, pp. 80-145, XP002301049.

Grohs B, et al. "Characterization of Flaw Location, Shape, and Dimensions with the Alok Systems" Materials Evaluation, Columbus, OH, US, vol. 40, No. 1, Jan. 1, 1982, pp. 84-89, XP009030157 ISSN: 0025-5327.

Olympus, "Olympus NDT Introduces a Manual Weld Inspection Solution That Includes conventional UT and Phased Array", http://www.ndt.net/search, Waltham MA, Apr. 23, 2008, NDT.net Issue: 2008-05, p. 1.

Olympus, "Phased Array Probe Update" Weld Probe Series (WPS), Innovation in NDT, 920-143A-EN, www.olympusNDT.com, PA_Probe_Update_WPS_EN_0804, Canada, 2006, pp. 1-2.

Olympus, "Phased Array Probe Update" AWS and DGS Probes, Innovation in NDT 920-144A-EN, www.olympusNDT.com, PA_Probe_Update_DGS-AWS_EN_0804, Canada, 2006 Olympus NDT, pp. 1-2.

Olympus, "Ultrasound, UT Phased Array, Eddy Current, and EC Array" OmniScan MX, Innovation in NDT 920-061E, OmniScan_MX_EN_0611, Canada, 2003-2006 Olympus NDT, www.olympusNDT.com, pp. 1-14.

Olympus, "Entry-Level Manual Phased Array Solutions", OmniScan M, Innovation in NDT 930-168, www.olympusNDT.com, OmniScanM_EN_0712, Canada, 2006 Olympus NDT, pp. 1-2.

Olympus, "Phased Array Ultrasound Probe Catalog" Innovation in NDT, www.olympustNDT.com, Fourth Edition, Nov. 2006, PA_Probe_Catalog_EN_0611, Canada, 2003-2006 Olympus NDT, pp. 1-24.

Olympus, "Manual Weld Inspection Solution" Convential and Phased Array UT, Innovation in NDT 920-135A-EN, www.olympusNDT.com, OmniScan_Manual_Weld_EN_0804, Canada, 2008 Olymput NDT, pp. 1-3.

RD Tech, "Phased-Array Ultrasound Probe Catalog 2005-2006", Third edition, May 2005, PA_Probe_Catalog_9505, Canada, 2004-2005 R/DTech Inc., www.rd-tech.com, pp. 1-24.

Olympus, "New Bei Olympus NDT: Ultraschallbilder Mittels Phased Array—Die Neuen Ultraschallprufgerate der EPOCH 1000 Serie", http://www.olympus.at/corporate/1696_3065.htm, Jan. 1, 2009, Hamburg, Jan. 2009, pp. 1-3.

RD Tech, "Ultrasound Phased-Array Transducer Catalog 2004-2005", R/D Tech Ultrasonic Transducers, Canada, 2004 by R/D Tech Inc., pp. 1-11.

Rd Tech, "Innovation in NDT" Nondestructive Testing, Panametrics-NDT, a business of D/D Tech Instrumnets Inc., NDT engineering corporation, R/D Tech Inc. Aug. 2004, pp. 1-15.

RD Tech, "Ultrasound Phased—Array Probe Catalog 2003-2004" www.rd-tech.com, First edition, Nov. 2003, PA_Probe_Catalog 1103, Canada, 2003, R/D Tech Inc., pp. 1-18.

* cited by examiner

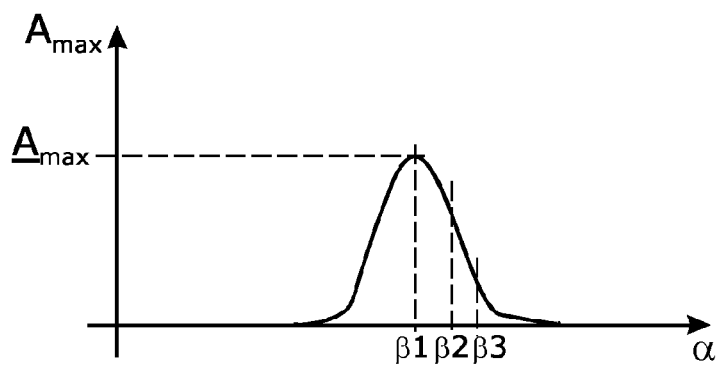
Fig. 3
Fig. 4
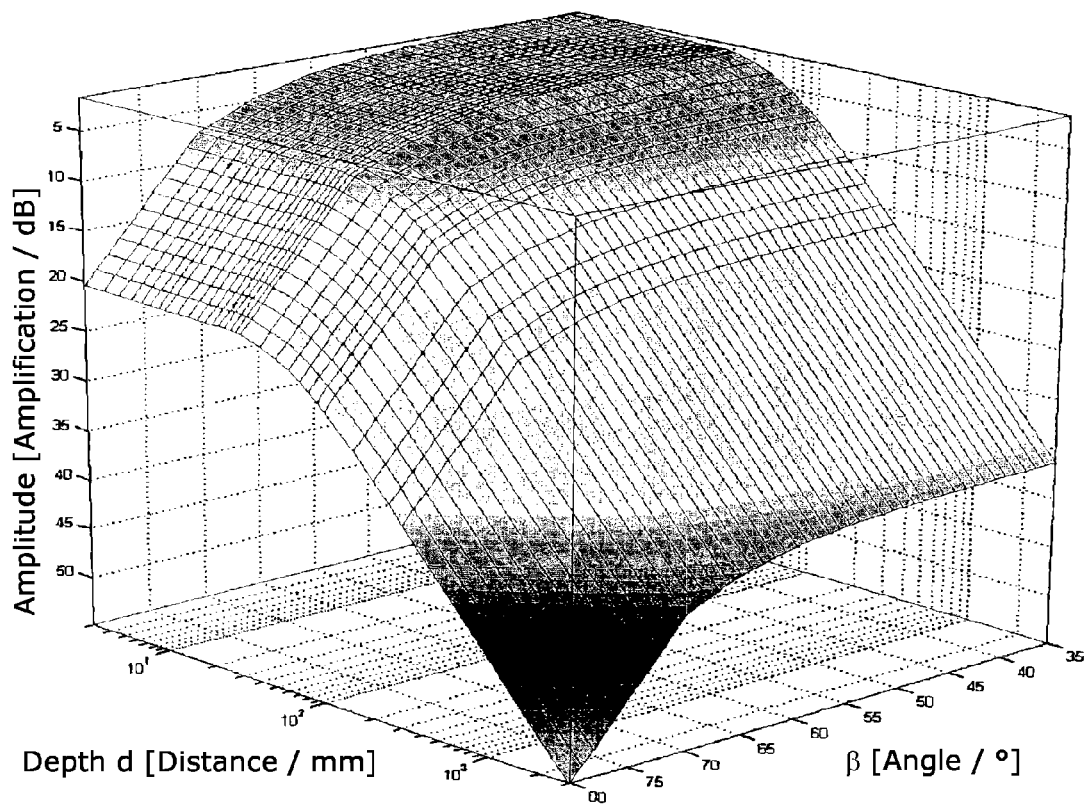

METHOD FOR THE NON-DESTRUCTIVE TESTING OF A TEST OBJECT BY WAY OF ULTRASOUND AND APPARATUS THEREFOR

TECHNICAL FIELD

The subject matter of the present invention is a method for nondestructive testing of a test object by means of ultrasound, whereby within the scope of the method, an equivalent reflector size is determined for an error in the volume of the test object by using ultrasonic echo signals that are recorded within the scope of the method. Further, the subject matter of the present invention is a device that is suitable for carrying out the method according to the invention.

BACKGROUND

Generic methods are well known in prior art. An error detected in the volume of the test object by means of an impulse echo method based on radiating pulsed ultrasound into the test object, for example, a cavity, an inclusion or also a crack, are characterized by stating a value for its equivalent reflector size ERG. The value of this equivalent reflector size is determined by a comparison of the amplitudes of the echo signals that are caused by the tested error in the volume of the test object, with the model of a comparative error of known size. In the so-called reference standard method, the test operator compares the echo signals of the tested test object with the echo signals which he obtains at a reference standard that is equivalent to the test object, which has one or more standard reflectors. For example, for this purpose, cylindrical bores with known dimensions can be inserted into the reference standard. The echo signals occurring at the bore during an ultrasound reflection that are obtained while testing the test object, are compared. In the reference standard method, the test operator therefore uses a suitable probe, that can be, for example, a suitable angle probe, measurements at the test object that is to be tested, as well as on the prepared reference standard.

In contrast, in the so-called AVG method, the amplitude of an echo signal resulting from an error in the volume of the test object is compared with a theoretically calculated and/or empirically determined echo signal of a model reference error, which is assumed to be a level circular disk, as a rule, and which is at the same depth in the test object as the error detected during the test of the test object. For this purpose, a so-called AVG diagram is prepared in advance for the probe used in the test, which contains the characteristics of the probe. The curves contained in the AVG diagram indicate the echo amplitude, which would be created by a reference error when measuring with the probe that is used. In a practical test problem, the test operator and then read the equivalent reflector size of the error detected in the volume of the test object by making a sound-attenuation correction (material-specific sound attenuation) and transfer correction (test object-specific injection losses) for the test object directly off the AVG diagram.

In a classic test method according to the AVG method, the test operator varies the probe position and orientation relative to the error found and tries to thereby maximize the resulting echo signal. This process is also described as "breeding" the ultrasound signal when testing materials by means of ultrasound. The actual determination of the equivalent reflector size of the detected error then takes place for the maximized ultrasound echo.

Additional details of the AVG method result, for example, from patent specification U.S. Pat. No. 5,511,425 A, which goes back to the legal predecessor of the applicant. Furthermore, the AVG method is described in detail in the book "Material Testing with Ultrasound", J. Krautkrämer and H. Krautkrämer, 5th edition, Springer Verlag, ISBN 3-540-15754-9, chapter 19.1, pages 343-349. The technical details concerning the AVG method revealed here are being added in their entirety to the revelation content of this application by means of this reference.

In its currently prevalent form, it is a disadvantage of the AVG method that for a meaningful characterization of an error in the volume of a test object, a test must be performed with a number of probes. This has its reasons therein, that for a given error, a perpendicular radiation into the test object does not necessarily supply a maximum echo amplitude. Rather, it depends on the orientation of the error in the volume of the test object at which irradiation angle a maximum echo signal can be obtained. In order to actually obtain a value for the equivalent reflector size of a detected error, that is reasonably correlated with the actual size of the error, therefore, as a rule, within the scope of standardized test procedures based on the AVG method, different angle probes are used which realize different irradiation angles. In practice, this method signifies significant testing and documentation effort for the test operator, so that as a rule, testing is only performed at a few irradiation angles. Beyond that the variation of the irradiation angle requires a change of the probe, which causes additional problems because of the never one hundred percent unambiguous calibration in addition to the connection properties of the probes.

BRIEF SUMMARY

The disclosure develop the AVG method in such a way that at least comparably meaningful test results can be obtained at significantly reduced test effort. Further, the invention provides a device that is suitable for carrying out the method in accordance with the invention.

The method in accordance with the invention is provided for nondestructive testing of a test object by means of ultrasound, and has at least the following procedural steps, which can also be performed cyclically:
  a) radiating directed ultrasonic pulses into the test object at an irradiation angle $\beta$, whereby the irradiation angle $\beta$ is electronically set,
  b) recording of echo signals that result from the ultrasonic pulses radiated into the test object, and
  c) determining an ERS value of an error in the volume of the test object from echo signals that can be associated with the error, whereby the influence of the electronic setting of the irradiation angle $\beta$ is compensated to the determined ERS value of the error by means of calculation.

The further development according to the invention of the generic AVG method is thus based on the use of a probe, in which the irradiation angle into the test object can be set electronically. Here, for example, a so-called "phased array probe" can be used, i.e. a probe that has a number of adjacently located ultrasound converters, which can be controlled phase-exact independently of each other. It is known from prior art, that in such phased array probes, the radiation angle $\alpha$ of the emitted sound beam can be varied freely within wide limits by targeted selection of the phase displacement between the individual ultrasound converters.

In accordance with the invention it is now provided, that in the calculation of the ERS value of the error, which was detected in the volume of the test object from echo signals that can be associated with the error, the influence of the electronic setting of the radiation angle $\alpha$ and thus the irradiation angle $\beta$ is automatically calculated and compensated to the determined ERS value of the error. The radiation angle and the irradiation angle $\beta$ are to be seen as being equivalent within the scope of the present invention, as they are physically firmly connected with each other. In particular, this means that within the scope of the method according to the invention, at least one of the following corrections takes place automatically, but preferably several:

- Compensation of the change of the virtual ultrasound converter size or the aperture of the ultrasound converter that is connected with it at a changing radiation angle $\alpha$ or irradiation angle $\beta$,
- Compensation of the change of the position of the injection point of the ultrasound radiated into the test object by the ultrasound converter at changing radiation angle $\alpha$ or irradiation angle $\beta$,
- Compensation of the change of the sound path in the delay block at changing radiation angle $\alpha$, and
- compensation of the position change of the focus in the test object at changing radiation angle $\alpha$ or irradiation angle $\beta$, Within the scope of the method according to the invention, in connection with the testing of a test object, as a rule, a measurement on one/several reference reflectors is made. These can, for example, be in the form of stud holes or horizontal bores, respectively with known diameter, that are inserted into the test body. The device that is suitable for carrying out the method according to the invention, which will be described in further detail in the following, thereby preferably provides the possibility for performing standardized calibration steps in which, for example, a selection can be made from a number of pre-set standardized test specimens.

For the electronic setting of the irradiation angle $\beta$, the previously cited phased array probes have particular advantages. But this does not mean that within the scope of the method according to the invention, other ultrasound probes with variable irradiation angle cannot also be used given the requirement, that the irradiation angle can be electronically set and also quantified.

For the calculation of the ERS value of the error detected in the volume of the test object from the echo signals, these are advantageously compared with a number of stored reference values, in particular with an AVG diagram for the specified, electronically set irradiation angle $\beta$. Thereby, this AVG diagram can have been advantageously determined in advance specific to the probe, for example, by having radiated several of various reference errors at the specified irradiation angle $\beta$, and a standard reference echo signal was generated form the resulting echo signals.

In a preferred further development of the method according to the invention, the procedural steps a) to c) are performed for at least two irradiation angles $\beta 1$ and $\beta 2$, which are respectively electronically set. In connection with performing these steps of the method that are developed further, the majority of the stored reference values then comes from different reference errors, which were respectively radiated at the at least two different irradiation angles $\beta 1$ and $\beta 2$. As a rule, the echo signals of the error detected in the volume of the test object are compared with two different arrays of curves of the AVG diagram that are respectively associated with irradiation angle $\beta 1$ or $\beta 2$.

In a preferred further development of the method in accordance with the invention, from the test data, in particular the echo signals obtained along a linear scan on the surface of the test object, a B-scan (X axis: position on the surface of the test object, Y axis: depth in the test object) is created. For this, the device used for performing the method according to the invention is provided with a displacement transducer, which captures the navigation of the probe on the surface of the test object. Thereby, the displacement transducer can work mechanically, but can also be based on optical or ultrasound signals that are analyzed according to the method of the "optical mouse". Thus, the device, in addition to the ultrasound signals recorded by the probe, also contains information about the position of the probe. By using both pieces of information, a B-scan is then created that can be shown on a suitable display unit or can be printed out as test protocol or can be electronically stored.

In particular, in the created B-scan, a detected error can be symbolized by a bar, the extent of which along its longitudinal axis correlates with the ERS value of the detected error. Advantageously, for the illustration of the ERS value and for the X position on the test object surface, the same scale is used. In the context of the present invention, any geometric figure is to be understood as bar, which has a mirror image with respect to two axes that are orthogonal with respect to each other, for example, a line, a rectangle, an ellipsis, etc. Thereby, in connection with the present invention, one of the two axes of symmetry of the bar is described as its longitudinal axis.

In order to increase the ability to interpret the B-scan produced within the scope of the method according to the invention, in particular to improve the ability to grasp the generated B-scan intuitively, it has been shown to be advantageous when at least one of the following additional characteristics of the detected error is shown in a suitable way in the generated B-scan:

a) the relative amplitude of the error echo,
b) the irradiation angle $\beta$, at which the ERS value of the detected error is at a maximum, for example, by illustrating the error as a bar that is perpendicular to the irradiation direction, at which the maximum error echo occurs,
c) the relative error size,
d) information concerning the sound path of the echo, for example, the leg from which the error echo emanates, and
e) information about whether the ERS value of the detected error is the same for all tested irradiation angles $\beta$ within the scope of specified error limits or if it is different.

The information of relative values can, for example, relate to measured reference values in connection with the test of the test object.

For this, one or several of the following display parameters can advantageously be used in the B-scan:

a) the color of the bar,
b) the dimension of the bar horizontal to its longitudinal axis (bar width B),
c) the angle of the longitudinal axis of the bar with respect to the surface of the test object, and
d) the basic geometric form of the bar.

By way of example, in the following, several illustration possibilities for different error characteristics are now explained in further detail.

Within the scope of the present invention, that information is to be understood as the relative amplitude of the error echo, as to whether the ultrasound echo caused by the error in the volume of the test object, i.e. the amplitude of the echo, exceeds a certain specified threshold. Such a threshold can, for example, relate to the measured error echo amplitude compared to the amplitude of the reference error. In particular, a threshold can then be stated in "millimeter ERS", for example, the ERS is to be larger than or equal to the registration limit of, for example, 2 millimeters or 5 millimeters.

If an irradiation angle $\beta$ is varied within the scope of the method according to the invention and that irradiation angle $\beta$ is determined at which the ERS value of the error is at a maximum, a reference point can then be given to the test operator concerning the orientation of the error in the volume of the test object by showing the longitudinal axis of the bar, which represents the error in the B-scan at an incline with respect to the surface of the test object. Advantageously, the bar is shown here in such a way that its longitudinal axis is perpendicular to the acoustic axis at those angles $\alpha$ of radiated ultrasound, for which the ERS value is at a maximum.

Additional information relevant for the test operator and the documentation is, whether the ERS value of the detected error is above or below a predetermined registration limit. Thus, it is possible, for example, to completely suppress error signals below a certain threshold in the generated B-scan. Alternatively, such error signals can also be color-coded or shown as transparent bars, in order to indicate the distance from the registration limit (e.g. in "mm ERS" or dB). In particular, the last two illustration variants offer the advantage that it can be pointed out to the test operator that although an error in the volume of the test object is present at the tested position, but that such is so small with respect to its ERS value that it does not need to be documented based on the pertinent test specifications.

Further, information as to from which sound path, i.e. "leg" of the radiating ultrasound beam the error echo results can be of interest to the test operator. This information is especially interesting when performing a test on a test object with coplanar surfaces, as here there is often a situation that the error is only captured by the ultrasound beam after such has been reflected at least once by the rear wall of the test object. This information can also be determined from the delay time of the error echo and can be, for example, shown to the test operator graphically by means of color-coding the bar.

Moreover, information as to whether the detected error in the volume of the test object is to be viewed as rather laminarly extended or as three-dimensionally extended error is of significance to the test operator. Three-dimensionally extended errors will be, as a rule, cavities or defects, which are due to the manufacturing process and which often do not represent any danger of fatigue failure. In contrast, laminarly extended errors are, as a rule, correlated with cracks in the test object, which can be symptoms of fatigue and which have a strong tendency to expand, which can lead to fatigue fractures. A three-dimensionally extended error in the volume of the test object is, within the scope of the method according to the invention, characterized thereby, that the resulting ERS value of the error is essentially independent of the irradiation angle. In contrast, two-dimensionally extending errors exhibit a strong dependence on the radiation angle. Thus, here, the information can be coded into the illustrated bar as to whether it is more likely a laminarly extending or a three-dimensional error. This can, for example, be done by adjusting the length and width of the bar that is shown or also by the selection of a geometric form that represents the symmetry of the error. But color-coding can also be used advantageously at this point.

Alternatively, the creation of a C-scan (X axis: position in the x direction on the surface of the test object, Y axis: position in the Y direction on the surface of the test object) or the creation of a sector scan (also S-scan, X axis: distance from the irradiation site/depth in the test object, Y axis: azimuthal angle: irradiation angle), can also be provided and be advantageous in special cases of application. All embodiments above for illustrating the determined error characteristics in the B-scan can be directly transferred to the additionally provided C-scans and S-scans.

The method in accordance with the invention allows, that the prescribed AVG method in many test specifications is now performed with modern ultrasound probes, that permit an electronic setting of the irradiation angle into the test object, for example, by using the phased array technique.

Of course, by implication it is possible to increase the number of the irradiation angles $\beta$, at which the equivalent reflector size ERS of an error is determined to practically to any number in order to increase the precision of the testing. In particular, the use of phased array probes allows continuous tuning of the irradiation angle $\beta$. In practice, the number of the different irradiation angles $\beta$ that can be set within the scope of a test objective is essentially limited by the effort, for example, of establishing AVG diagrams.

A device in accordance with the invention for nondestructive testing of a test object by means of ultrasound comprises a transmitter probe with an ultrasound transmitter that is equipped to radiate directed ultrasonic pulses at an irradiation angle $\beta$ into a test object. Further, the device comprises an ultrasound receiver, which is equipped to record echo signals of the ultrasonic pulses radiated into the test object. Further, the device comprises a control and analysis unit that is equipped to control the ultrasound transmitter of the transmitter probe in such a way that the ultrasound transmitter is excited into emitting a sequence of ultrasonic pulses. Further, it is equipped to process the echo signals recorded by the ultrasound receiver. Finally, it is equipped to determine the ERS value of the error from the recorded echo signals that can be associated with an error in the volume of the test object. In accordance with the invention, the ultrasound transmitter now comprises a number of independently controllable ultrasound converters, i.e. it is of the phased array type. Correspondingly, the control and analysis unit is equipped to control the majority of ultrasound converters of the ultrasound transmitter individually, phase-exact in such a way that the radiation angle $\alpha$ of the ultrasound transmitter can be electronically adjusted in a targeted manner. As a consequence of the variation of the radiation angle $\alpha$, the irradiation angle $\beta$ of the ultrasound into the test object can thus also be electronically adjusted.

Finally, the control and analysis unit is equipped to automatically compensate the influence of the electronic adjustment of the irradiation angle $\beta$ to the ERS value of the error that is to be determined.

As previously explained in connection with the method according to the invention, the ERS value of an error can, for example, be automatically determined by comparison with a number of the stored reverence values, whereby these reference values can be, for example, one or more AVG diagrams. In this connection it is pointed out that for the determination of an ERS value of an error detected by means of the method in accordance with the invention, for each angle at which the error is irradiated, in addition to an AVG diagram, a reference echo, for example, from a test specimen, must also be available.

In a preferred further development of the device in accordance with the invention, the control and analysis unit is therefore equipped to electronically set at least two different irradiation angles $\beta$. In this case, the reference values stored in the control and analysis unit are correlated with the at least two different irradiation angles $\beta$. In particular, these can be two AVG diagrams specific to the probe or an AVG family of curves for the electronically set two different irradiation angles $\beta$.

In a particularly preferred embodiment, in the control and analysis unit, a number of reference values are stored, for example, in the form of AVG diagrams that are correlated in groups with different irradiation angles β. Thereby, these reference values can continue to be specific to the probe. In particular, it can thus be a number of AVG diagrams specific to the probe for different irradiation angles β. Preferably, the probe continues to be provided with an electronic identification that makes it possible for the control unit to independently recognize the type of probe or even the individual probe upon connection of the probe and to select the stored probe (type)-specific reference values.

In all embodiments, however, the determination of an (irradiation angle-specific) ERS value for a detected error has, as a rule, the prerequisite, that a reference value is present that was captured, for example, by a probe at the respective angle, or comes from an interpolation between different measured angles.

In a particularly preferred embodiment of the device in accordance with the invention, its control and analysis unit is equipped to automatically convert from radiation angle α of the ultrasound transmitter to the irradiation angle β that results in the test object in order to automatically compensate the influence of the electronic setting of the irradiation angle β to the ERS value of the error that is to be determined. In particular, this compensation can be designed to be probe-specific. Beyond that, it is practically equipped to consider the ultrasound-specific properties of the material of the delay block and the test object such as, for example, the speed of sound.

A further improvement can be achieved when for the automatic compensation of the influence of the electronic setting of the irradiation angle β to the ERS value of the error to be determined, the control and analysis unit of the device in accordance with the invention is equipped to automatically compensate the variation of the virtual ultrasound transmitter size and thus the aperture of the probe that accompanies the electronic variation of the irradiation angle β. The virtual ultrasound transmitter size results from a projection of the actual geometric dimension of the ultrasound transmitter onto a radiation direction that is perpendicular to the electronically set radiation direction of the ultrasound transmitter. If the ultrasound transmitter radiates at a radiation angle α that is different from 0°, this has the direct consequence of an acceptance of the virtual ultrasound transmitter size. As the ultrasound transmitter size is perhaps included in the determination of the ERS value of the detected error, here, if necessary, a corresponding automatic compensation must take place.

A further improvement results when the control and analysis unit is equipped to automatically compensate the influence of the displacement of the injection site $X_0$, that accompanies an adjustment of the radiation angle α or the irradiation angle β, to the ERS value of the error that is to be determined.

Finally, an automatic compensation of the position change of the focus in the test object can also be provided, which results when the radiation angle α is changed due to the change in the sound path length that results from it in the delay block.

In conclusion, let it be pointed out that the automatic compensation in accordance with the invention of the influence of the electronic adjustment of the irradiation angle β to the ERS of the error that is to be determined, can be performed in two different ways based on the stored AVG diagrams. On the one hand, the control and analysis unit can be equipped to standardize the actual measured values (i.e. time-resolved echo signals) by considering the influence of the adjustment of the irradiation angle β, i.e. for example, to convert to the results of a conventional probe with fixed irradiation angle β. These are then compared with a standardized AVG diagram.

On the other hand, during the creation of the AVG diagrams that are stored in the control and analysis unit, the probe-specific influences of the electronic angle adjustment to the echo signals can already be considered, i.e. in the stored AVG diagrams already, the compensation that is to be performed is considered already. Even this implementation is to be comprised by the method according to the invention, as well as the device in accordance with the invention.

Finally, in a preferred further development, the device in accordance with the invention also comprises a display unit, which is controlled by the control and analysis unit. Thereby, the control and analysis unit is equipped, to at least show a B-scan of the test object on the display unit of the device. Preferably, a possibility is also provided to create a C-scan, as well as a sector scan (S-scan) of the test object and, for example, show it on the display unit. The possibilities of illustrating the result of the test method performed by means of the device in accordance with the invention on the display unit, were already explained in detail in connection with the explanation of the method in accordance with the invention. Reference is hereby made to these explanations.

Even those additional error characteristics, which can be also be shown advantageously in a B-scan, as well as the possibilities of coding these characteristics in the B-scan, was addressed already in detail in connection with the explanation of the device in accordance with the invention.

BRIEF DESCRIPTION OF THE DRAWINGS

Additional advantages and characteristics of the device in accordance with the invention as well as the method in accordance with the invention result from the subordinate claims and the examples of embodiments, which are explained in the following in further detail in conjunction with the drawings.

Shown in the drawing are:

FIG. 3: an illustration of the maximum echo amplitude A max depending on the irradiation angle β, FIG. 4: an angle-resolved probe-specific AVG diagram.

DETAILED DESCRIPTION

Figure 1:
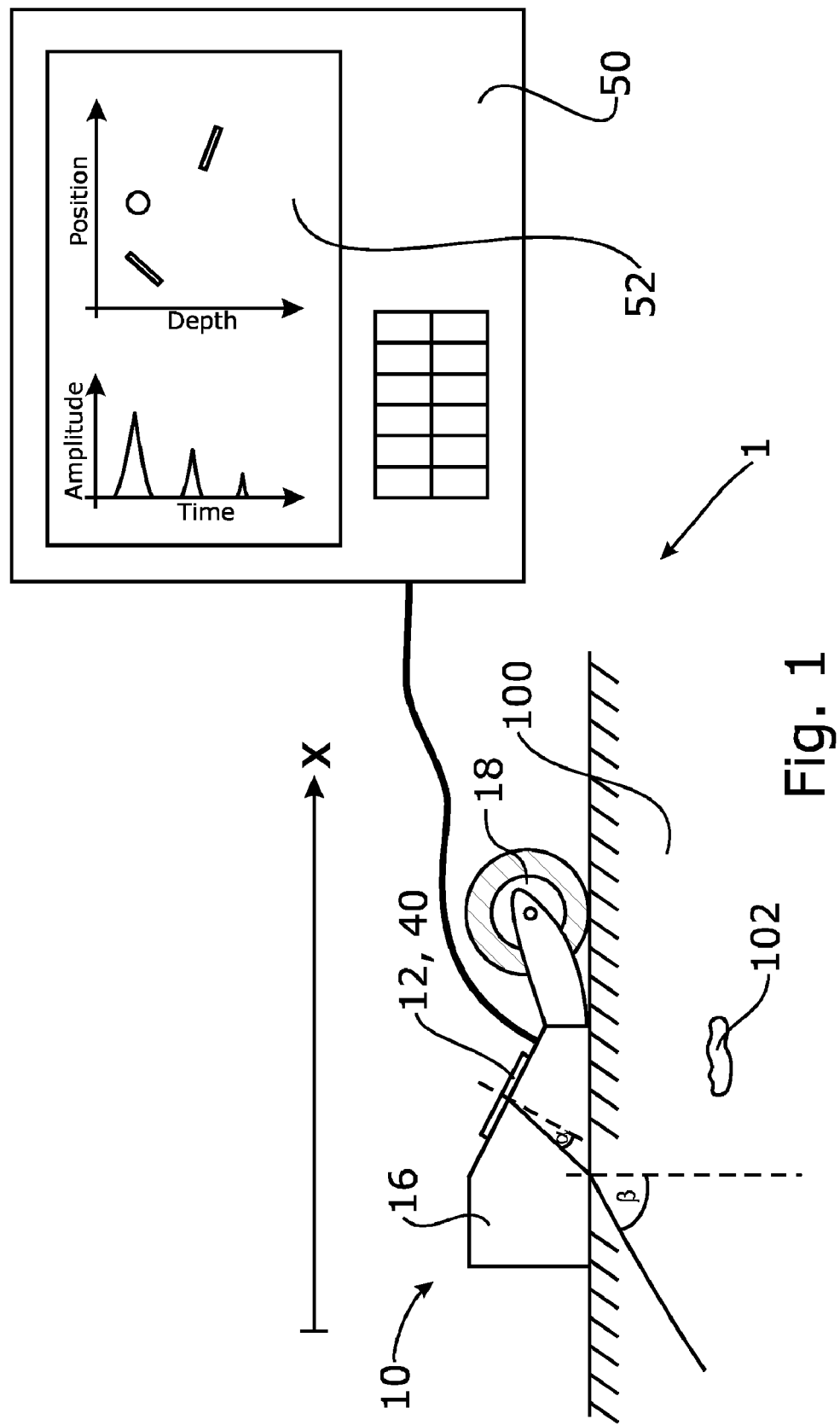
FIG. 1: a schematic illustration of the device in accordance with the invention for nondestructive testing of a test object.

FIG. 1 shows an example of an embodiment of device 1 according to the invention for nondestructive testing of a test object 100 by means of ultrasound. The device 1 comprises a transmitter probe 10 that in turn has a delay block 16 and an ultrasound transmitter 12 that is mounted on such. The ultrasound transmitter 12 is thereby mounted onto the delay block 16 in such a way that upon an excitement of the ultrasound transmitter 12 to emit ultrasonic pulses, these are essentially injected into the delay block 16. The delay block 16 can thereby be formed, for example, by a body made of Plexiglas®, as it is known, in principle, in prior art. Preferably, the elements of the transmitter probe 10, are put together in a joint housing, which is not shown in the figure for reasons of clarity. The illustrated transmitter probe 10 is an angle probe that is provided for injecting the ultrasonic pulses transmitted by the ultrasound transmitter 12 at an angle of incidence 13 that is measured with respect to the surface normal of the entry surface of the test object 100, into test object 100. The use of angle probes is optional and not mandatory, depending on the application, probes for a perpendicular irradiation (i.e. $\beta=0°$) can also be used.

The ultrasound transmitter 12 that is used in transmitter probe 10 is an ultrasound transmitter of the phased array type, i.e. the ultrasound transmitter 12 comprises a number of ultrasound converters 14, that form at least one linear configuration and which are individually controllable. The longitudinal axis of the at least linear array of the ultrasound converters 14 is thereby oriented into the direction labeled X. By means of targeted adjustment of the phase position between the individual ultrasound converters 14 it is possible to dynamically influence the radiation angle $\alpha$, i.e. the direction of radiation within wide limits.

In the shown example of an embodiment, the transmitter probe 10 comprises a mechanical displacement transducer 18 that mechanically senses the displacement of the transmitter probe 10 on the surface of the test object 100, and makes corresponding position information available, for example, to a control unit 50 that is connected with the transmitter probe 10. Alternatively, the displacement transducer 18 can also work contactless, for example, according to the principle of an optical mouse. The displacement transducer 18 is—independent of its design—preferably in a position to detect the displacement of the transmitter probe 10 on the surface of the test object 100 in two directions that are independent of each other. Special advantages result when the rotating motions of the transmitter probe 10 can also be detected on the surface of the test object. Based on the technology that is revealed in the patent specification U.S. Pat. No. 7,324,910 B2, as well as its further development, which is revealed in the German patent application, file number 10 2007 028 876.1 dated Jun. 26, 2007, a separately formed displacement transducer can be dispensed with completely, as all of the position information can be obtained from the signals of the ultrasound transmitter 12 itself.

A control unit 50 is connected with the transmitter probe 10, which is equipped to individually control the ultrasound converters 14 individually phase-exact, that are located in the ultrasound transmitter 12 of the transmitter probe 10. Further, the control unit 50 is equipped to be connected with an ultrasound receiver 40, in order to receive echo signals that are reflected back by a test object 10, which result from ultrasonic pulses that have been irradiated by the ultrasound transmitter 12. In the example of an embodiment shown at present, the ultrasound transmitter 12 located at the transmitter probe 10 also serves as ultrasound receiver 40. For this purpose, the separately formed and individually controllable ultrasound converters 14 that are contained in ultrasound transmitter 12, are electrically interconnected to a large-area ultrasound transmitter 12 after sending a transmitting pulse, which then functions as ultrasound receiver 40. Of course, it is also possible to use a separately formed ultrasound receiver 40, which, for example, can be located in a separately formed receiver probe. Such a separate receiver probe would, in the present example of an embodiment, further also contain a delay block, corresponding to the delay block 16 of transmitter probe 10.

For nondestructive testing of a test object 100, for example, for errors 102 that are hidden in the volume of the test object 100, the transmitter probe 10 is connected with the control unit 50 and placed onto the surface of the test object 100. The acoustic coupling of the transmitter probe 10 onto the test object 100 takes place, as a rule, by using a suitable coupling means, which can, for example, be water, oil or also a water-based gel.

The test object 100 is preferably a mechanical work piece or tool, but it can also be a biological specimen.

Now, the test operator moves the transmitter probe 10 to and fro along the direction that is marked by X in FIG. 1 on the surface of the test object 100. At the same time, the test operator observes the display on a display unit 52 that is associated with a control unit 50, which is integrated into the control unit 50 as display in the shown example of an embodiment. An A-image is shown on display unit 52 in the illustrated example of an embodiment, in which the amplitude of the ultrasonic pulses that are reflected back are shown for the specified irradiation site X as a function of time. If the sound beam sent by the transmitter probe 10 impinges on an error 102 in the volume of the test object 100, i.e. on a structure that reflects ultrasound such as a defect, cavity or a crack, a part of the irradiated sound beam is reflected back and comes back along the same path to the ultrasound transmitter 12 of the transmitter probe. As mentioned, it simultaneously functions as ultrasound receiver 40 that converts the sound signal that is reflected back into an electric signal which then, if appropriate, is enhanced in suitable manner and emitted to the control unit 50. In the control unit 50, the echo signal that was received, which, as a rule, is present as an electrical signal, but which can, for example, also be transmitted by the transmitter probe 10 in the form of an optical signal, is processed in a suitable way, which can, for example, take place by means of highly time-resolved AD conversion and signal processing. In the following, the signal is shown on display unit 52 in the form of the A-scan as described above. If the irradiated ultrasound beam impinges on an error 102, this results in echo signals, which are directly visible in the A-scan. The previously described mode of the procedure thereby preferably takes place at a fixed irradiation angle $\beta$.

Figure 2A:
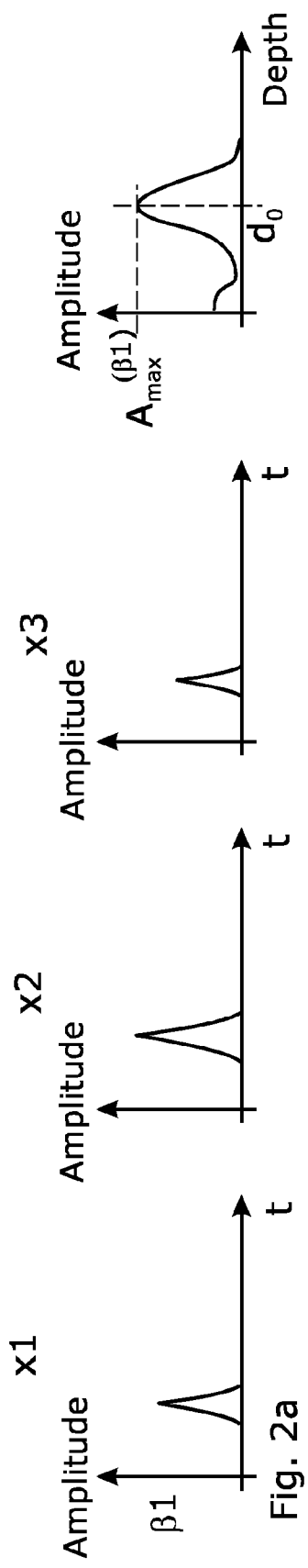
FIG. 2a-2c: an A-scan of the test object, recorded at different irradiation positions x, as well as at different irradiation angles β, as well as the propagation of the maximum amplitude A max for a given irradiation angle β dependent on the depth d in the test object.

In the event the test operator has detected an error 102 using the operating mode previously described, he then attempts, by variation of the X position of the transmitter probe 10 on the surface of test object 100, to maximize the amplitude of the resulting error signal, i.e. to breed the signal. This breeding of the signal also takes place for a fixed irradiation angle $\beta$ 1. The A-scans that result during the breeding of the echo signal at various irradiation sites X1, X2 and X3 are shown in FIG. 2a. It becomes clear that because of the change of the path in the test object 100, the echo signal occurs at different times, but beyond that, is also varies in its maximum amplitude. This is due to the fact that during the displacement of the transmitter probe 10 on the surface of the test object 100, the center of the sonic cone, in which the highest sonic pressure predominates, is moved over error 102. As a rule, the maximum amplitude in the echo signal results when the sound beam impinges centrally onto error 102. If one determines the enveloping echo signal of all echo signals for a fixed irradiation angle $\beta$ 1 at a variation of the irradiation site X, one obtains an illustration of the echo amplitude as function of the delay time or the depth of the error 102 in test object 100, as it is clearly shown in the diagram on the right of FIG. 2a. Using this diagram, the maximum echo amplitude A max ($\beta 1$) can be determined, which results for the selected irradiation angle $\beta$ 1.

Figure 2B:
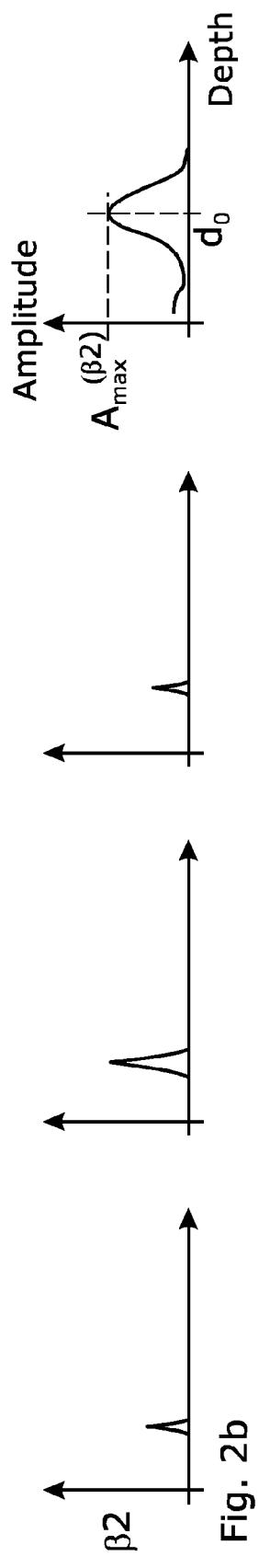

After that, the test operator can vary the irradiation angle $\beta$ so that he once again performs the same examination for a different irradiation angle $\beta$ 2. Alternatively, an automatic change of angle is possible within the scope of a partially automated testing method. From this as well, a diagram results for the propagation of the amplitude as function of time or the depth of the error 102 in test object 100. Such a diagram is shown in FIG. 2b on the right. The maximum echo amplitude that results here for irradiation angle $\beta$ 2 does not absolutely have to correspond to the echo amplitude for the irradiation angle $\beta$ 1 that was selected first, as a rule, actually a deviation will be present here, to the extent it is not a continuously shaped error.

If the various delay times that result on account of the different irradiation angles $\beta$ 1 and $\beta$ 2 are compensated, the peaks in the cited illustration of the enveloping A max ($\beta$) are essentially at the same position $D_0$. However, if one dispenses with such a delay time compensation, the peaks occur at different positions.

Figure 2C:
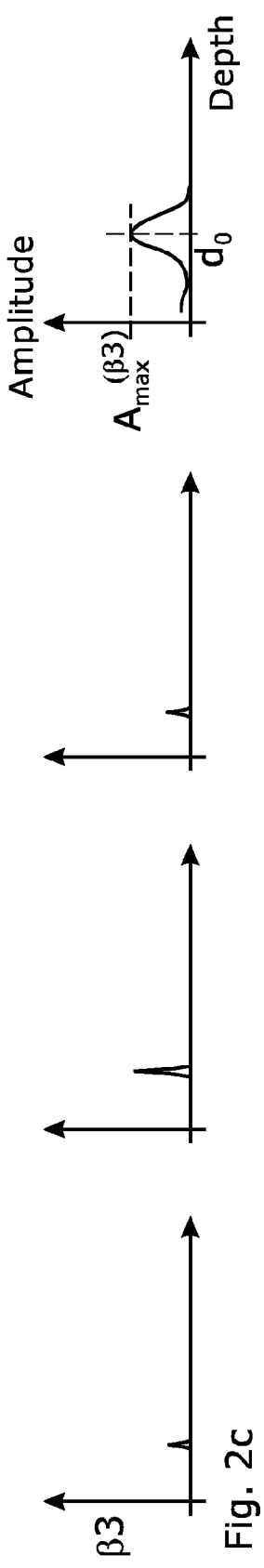

In FIG. 2c, the result of the same method for a once again changed irradiation angle $\beta$ 3 is shown by way of example.

The irradiation angle $\beta$ is electronically tuned in the operating mode described above by utilizing the advantageous transmitting properties of an ultrasound transmitter 12 that is of the phased array type.

In an alternative embodiment, the control unit 50 is equipped to automatically optimize a potentially resulting echo signal for a specific irradiation site X, by varying the irradiation angle $\beta$.

If one enters the maximum amplitudes A max resulting for various irradiation angles $\beta$ above the corresponding irradiation angle $\beta$, one receives a diagram as it can be seen in FIG. 3. From this diagram or from the echo data on which it is based, now that irradiation angle $\beta$ can be determined, for which the tested error 102 exhibits the maximum echo amplitude A max. From this as well, the angle-dependence of the ultrasonic reflectivity of the error 102 can be illustrated and analyzed in an easy way. Potential interpretations of the behavior obtained with respect to the type of the error 102 have already been addressed above.

In advance of the previously explained practical test of the test object, so-called AVG diagrams are created, as it is known in prior art for probes with fixed irradiation angle $\beta$. Thereby, an AVG diagram shows the echo amplitudes of circular disk reflectors with various diameters and also of an extended, level reflector (back wall echo) as function of the distance, i.e. as function of the depth d in the test object. In contrast to the AVG diagrams known in prior art and devices for measuring ultrasound, in which probe-specific AVG diagrams are stored, for example, in digital form, within the scope of the present invention, the AVG diagrams are in addition recorded angle-resolved or generated and are, if necessary, stored in control unit 50. By way of an example, FIG. 4 shows such an AVG diagram for a specified diameter of a circular disk reflector as a function of the distance d and a function of the angle $\beta$.

For the determination of the ERS value of an error with the help of a phased array probe, which allows an electronic variation of the irradiation angle $\beta$ into the test object 100, an adaptation of the AVG diagrams generally known from prior art (compare U.S. Pat. No. 5,511,425 A), which is based on theoretical considerations, could be required in various respects. On the one hand, in general, a calibration of the probe-specific AVG diagram is required in order to take the ultrasound properties of the material of the test object into consideration and to compensate the probe-specific effects such as a change of the ultrasound converters or a changed coupling of the transmitter probe to the test object. To do so, prior to performing the actual testing of a test object 100, most test specifications require that a calibration step be performed, in order to calibrate the general AVG diagram, which can already be stored in the device 1.

Beyond that, in an electronic variation of the irradiation angle $\beta$ it is to be considered with the help of a phased array probe that the ultrasound properties of the probe change directly as a result of the angle change. For this reason, the general AVG diagram, which was determined for a certain irradiation angle must be converted to other (electronically set) irradiation angles $\beta$. In particular, it is possible to perform this conversion in the device itself, so that storage of a number of probe-specific AVG diagrams for various irradiation angles $\beta$ is not required. In an alternative approach it is, of course, also possible to store a number of, for example, probe-specific AVG diagrams in device 1 that relate to a number of irradiation angles $\beta$. Here too, the AVG diagrams can be determined empirically or they can be calculated theoretically.

Figure 5:
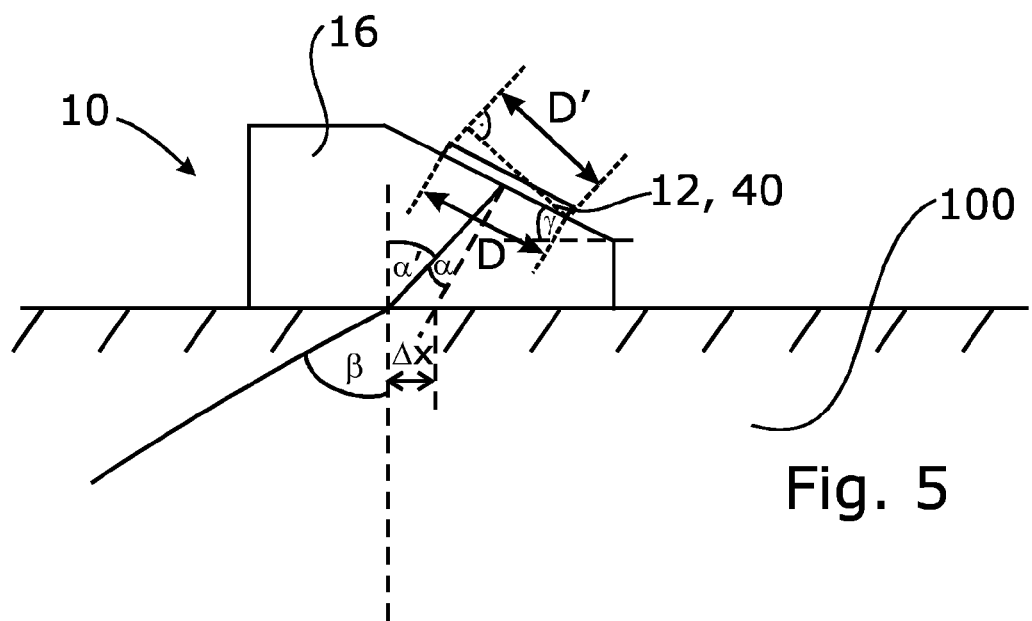
FIG. 5: a schematic illustration of the beam geometry at the probe.

As has already been explained above, when using a device in accordance with the invention, the irradiation angle $\beta$ can be electronically tuned. As can be seen in FIG. 5, for example, in an angle probe with a delay block, in an electronic tuning of the irradiation angle $\beta$, the injection point of the sound beam into the test object changes by $\Delta X$, as well as also the diameter of the sound beam at its transition from the delay block into the test object. This can also be interpreted as a virtual change of the dimensions of the ultrasound transmitter 12 (D→D'), which must also be considered when preparing the AVG diagrams cited above. By means of simple geometric considerations, as well as the acoustic laws of calculation, it is possible in an easy way to calculate the influence of the electronic change of the irradiation angle $\beta$ on the change of the injection point and the size of the virtual ultrasound transmitter (12).

In order to now determine the equivalent reflector size ERS for the error detected in the volume of the test object, the test operator—just as in the known devices in prior art with probes with fixed irradiation angle $\beta$—lets that AVG curve be displayed on the display unit 52 of control unit 50, which corresponds to the electronically selected irradiation angle $\beta$, at which the maximum echo signal A max had resulted. Thereby, the AVG curve received $\overline{a}$ basic calibration in advance of the actual measurements of reference errors, which can, for example, be inserted into the test specimen. The "basic calibration" is a calibration of the sensitivity of the probe used. As a rule, the reference echo that is required for this is obtained from rear wall echoes at the standardized so-called "K1" or "K2" test specimens (depending on the frequency of the probe used). As there are no level rear walls in these cases, a circular arc correction (as a rule, indicated by the manufacturer of the probe) must also be performed. On the other hand, reference reflectors out of a component are rather infrequent.

The AVG curve shown on the monitor corresponds to a specified equivalent reflector size, which, as a rule, corresponds to the registration limit prescribed by the test specifications. If an error is detected, the echo of which exceeds the AVG curve shown on the monitor, for example, the control unit 50, for example, automatically indicates (either in dB above the registration limit or directly in millimeters) the resulting equivalent reflector size ERS. In an AVG curve, the test operator thus can, directly read off the equivalent reflector size ERS of the error by stripping the delay time of the pulse up to the detected error.

In a largely automated testing routine, the test operator scans the surface of the test object 100 using the procedural mode described above until he finds echo signals that are due, in his opinion, to an error 102 in the volume of the test object 100. If necessary, he manually performs a certain optimization of the error signal before he resets the control and analysis unit 50 of the device 1 in accordance with the invention to an automatic measuring mode. In it, the control unit 50 controls the ultrasound transmitter 12 in such a way that the injection point of the sound beam into the test object is displaced in the X direction on the surface of the test object 100. At the same time, the control unit 50 captures the amplitude of the resulting error echo as function of the injection point and determines the maximum echo amplitude. Thereby, the irradiation angle $\beta$ is kept constant.

In one of the following steps of the method, the control unit 50 varies the irradiation angle so that the error 102 that is to be measured in the volume of the test object 100 is irradiated at a different angle $\beta 2$. Here too, the control unit 50 varies the injection point of the emitted sound beam into the test object by means of suitable control of the ultrasound transmitter 12, whereby simultaneously, the resulting echo amplitude is captured. Here too, the maximum echo amplitude A max ($\beta 2$) is determined for the set irradiation angle $\beta 2$, i.e. the test operator "breeds" the echo signal.

By comparison with one or several probe-specific as well as angle-specific AVG diagrams, the control unit 50 of the device in accordance with the invention then automatically determines the ERS value of the measured error 102. To do so, the control unit 50 automatically compensates the influence of the electronic variation of the radiation angle $\alpha$ of the ultrasound transmitter 12 onto the injection point of the ultrasound beam into the test object and thus onto the delay time of the ultrasonic pulses from the ultrasound transmitter 12 up to the error 102. Further, control unit 50 also automatically compensates the influence of the electronic variation of the radiation angle $\alpha$ of the ultrasound transmitter 12 to the virtual transmitter size, as was described above. Even the change in position of the focus in the test object due to the changed sound path in the delay block is automatically compensated by the control unit 50. Finally, the control unit 50 automatically converts from radiation angle $\alpha$ to irradiation angle $\beta$, whereby, if necessary, the material properties of the test object are considered as well.

As the result, from the manual as well as from the automatically performed test method an ERS value of the error 102 that is detected in the volume of the test object is obtained, as well as that irradiation angle $\beta$ at which the maximum error signal $\underline{A}$ max results. These data can be recorded.

Figure 6:
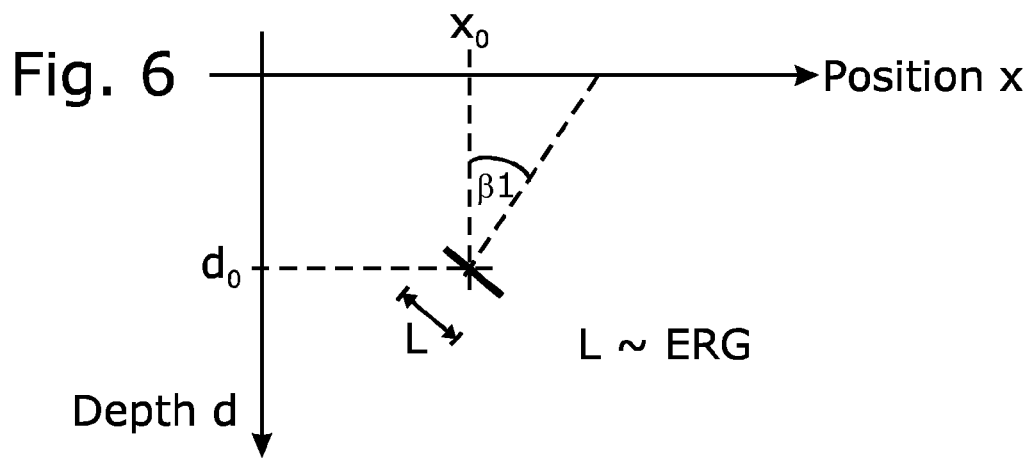
FIG. 6: an illustration showing a B-scan of the specimen, in which an error is illustrated by an associated ERS value.

If additional position information is available for the probe, the test result can further be illustrated in a clearly demonstrative way in a B-scan, such as it is shown in FIG. 6, for example, or also in a C-scan or S-scan. Thus, a bar of length L can be shown in the B-scan, the X position of which on the surface of the test object corresponds to that $X_0$ position, at which the error is located as per calculation. In the Y direction, the bar is located at depth $D_0$, which corresponds to the calculated depth of the error in the volume of the test object 100. Further, the length L of the bar, which demonstrates the measured error 102 is directly interlinked with the equivalent reflector size ERS of the error that was determined within the scope of the testing method in accordance with the invention. Beyond that, advantageously, the orientation of the bar is directly correlated with that irradiation angle $\beta$, at which the maximum echo signal A max results. For this, the longitudinal axis of the bar can $\overline{be}$ shown at an incline with respect to the X axis in such a way that the bar is oriented perpendicular to the sound propagation direction that corresponds to that irradiation angle $\beta$, at which the maximum echo signal results. The orientation of the bar in the B-scan shown in FIG. 6 thus directly provides the test operator information about the orientation of the measured error in the test object, which can also be recorded and stored. Thereby, the schematically shown B-scan in FIG. 6 is preferably also shown to the test operator on display unit 52, which is connected with control unit 50. Preferably, the control unit 50 is equipped to transfer the stored data to a PC, where the data can be subjected to additional analysis.

Figure 7:
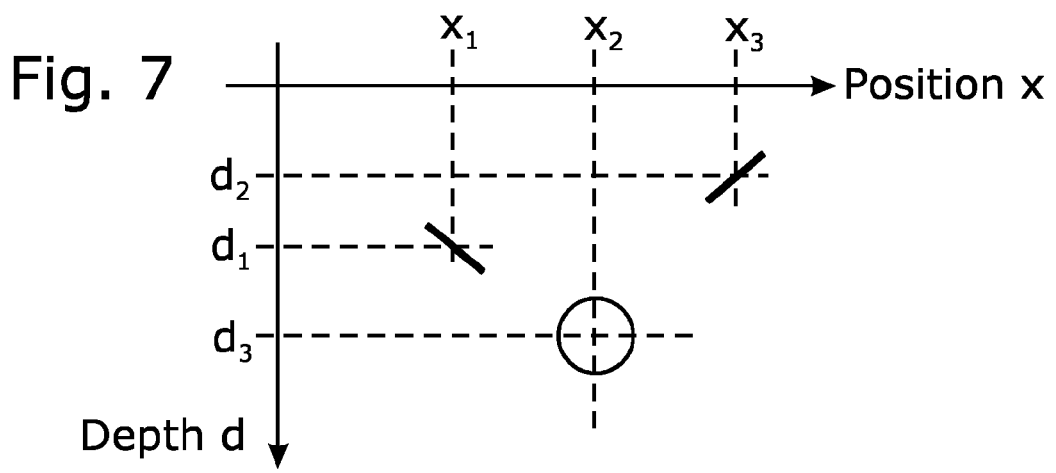
FIG. 7: an illustration corresponding to FIG. 6 of the test object with a number of errors that have different reflection properties.

Finally, FIG. 7 shows an additional B-scan of a test object 100, in which three errors 102 can be seen in the volume of the test object 100. Thereby, the errors are at positions X1, X2 as well as at X3. The errors 102 detected at positions X1 and X3 thereby exhibit a strong dependence of the echo signals on the irradiation angle, i.e. the variation resulting from the maximum error echo amplitude A max exceeds a certain threshold when the irradiation angle $\overline{\beta}$ is changed. From this it can be concluded, that it these are more likely laminarly extending errors 102; correspondingly, these errors are shown in the B-scan of FIG. 7 as essentially one-dimensional symbols.

The error 102 detected at position X2, on the other hand, shows an echo amplitude that is essentially independent of irradiation angle $\beta$, i.e. the variation of echo amplitudes that results remains below a predetermined threshold. Based on this, it can be concluded that it is more likely to be a uniform three-dimensional extension of the error 102, which is shown in the B-scan of FIG. 7 by a two-dimensional error symbol (e.g. a circular disk as shown), the diameter of which is correlated with the equivalent reflector size ERS of this error.

Figure 8:
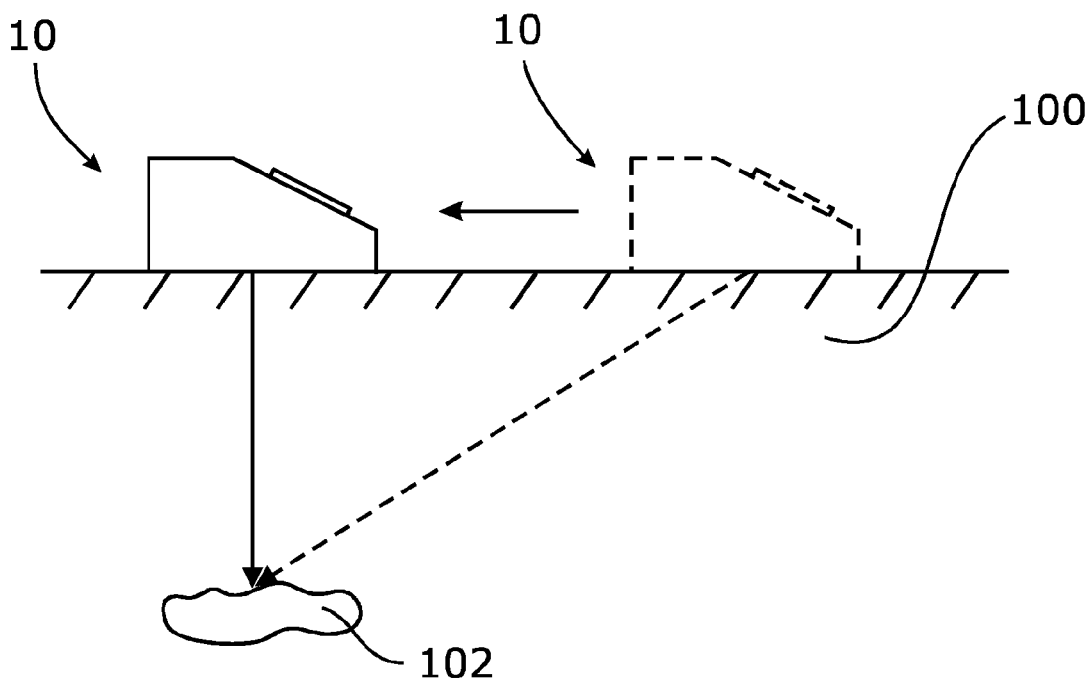
FIG. 8: a schematic illustration of a method for capturing the angle-dependence of the ERS value of an error in the volume of the test object.

In conjunction with FIG. 8, a novel method is now illustrated, which is likewise implemented into the device 1 in accordance with the invention. In a first procedural step, the transmitter probe 10 is controlled by device 1 in such a way, that the ultrasonic pulse radiates at a fixed irradiation angle $\beta$ into test object 100. If the test operator has detected an error 102 in the volume of the test object 100, he breeds the error signal until the signal amplitude is at a maximum. In a next step, he activates a "scan" function in which the probe 10 is controlled by device 1 in such a way that the irradiation angle $\beta$ into the test object 100 is electronically varied within a specified interval. The device 100 [Translator's note: Should probably be device 1.] is further equipped to determine the maximum error echo and the associated irradiation angle $\beta$ Max from the error echoes received at various irradiation angles $\beta$. If the position of the transmitter probe 10 is changed on the surface of the test object 100, a changed irradiation angle $\beta$ results, at which the error echo is at a maximum, as a maximum error echo is obtained as a rule then, when the error is captured centrally by the ultrasound beam. If, as described previously, an electronic angle scan is performed, the device 1 can fully automatically find that changed irradiation angle $\beta$, for which the error echo goes to the maximum. By means of a variation of the position of the transmitter probe 10 on the surface of the test object 100, by using the previously described method, the maximum error echo can automatically be determined for various irradiation angles $\beta$. Thereby, the position of the transmitter probe 10 can be performed on the surface of the test object 100 on the one hand by a mechanical motion of the transmitter probe 10, but it can also be varied virtually by executing a linear scan within a number of individual ultrasound converters 14 in ultrasound transmitter 12 (a so-called "electronic linear scan").

If at least one AVG diagram is stored in the device, according to FIG. 4 that calculates theoretically, for example, or which can have been determined by means of practical measurements, then from the diagram of the determined maximum error echo amplitudes for a certain irradiation angle β, the ERS value of the error can be determined for this angle. If applicable, it can be required that the AVG diagram/s stored in the device are calibrated probe-specific or material-specific by using the reference echo obtained at a probe, which is perhaps recorded at different irradiation angles before the actual test of the test object 100 is performed. The AVG method thus in particular permits the automatic compensation of the sound paths due to the different irradiation angles that result in the test object.

Alternatively, during the determination of the angle-dependent ERS value of an error 102 in the volume of the test object 100, the device 1 can also refer back to the position information that is supplied by the displacement transducer unit 18. As described above, in a first step for a fixed irradiation angle β, that position of the transmitter probe 10 on the surface of the test object 100 is looked for, at which the amplitude of the error echo is at a maximum.

After that, the test operator activates a "trace" function at device 1. If it is activated, device 1 is equipped to set that irradiation angle β at the transmitter probe 10 when the position of the transmitting probe 10 changes, by means of suitable geometric calculations, at which the error 102 in the test object is captured centrally by the ultrasound beam even at a changed position of the transmitter probe position. When the transmitter probe 10 is displaced on the surface of the test object 100, the detected error 102 is then at all times captured centrally by the ultrasound beam with the help of the cited trace function, so that the resulting error echo can be viewed as the maximum error echo for the set irradiation angle β. Thus, directly by varying the position of the transmitter probe 10 on the surface of the test object 100, the maximum error echo can be recorded as a function of the irradiation angle β, and from this, the angle-dependent ERS value of the error 102 can be determined as a function of the angle β.

Figure 9A:
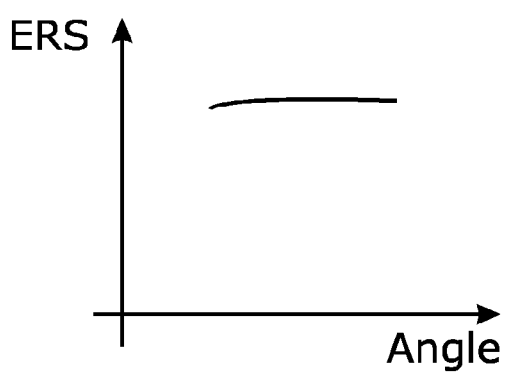
FIG. 9a, 9b: schematic illustrations of the angle-dependent ERS value of two different errors in the volume of the test object.
Figure 9B:
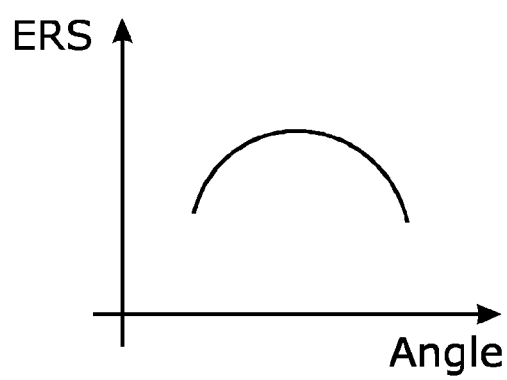

FIGS. 9a and 9b finally show, by way of example, the propagation of the angle-dependent ERS value of two different errors 102 in the volume of the test object 100. Thereby, FIG. 9a shows an error 102, the ERS value of which varies only slightly with the irradiation angle β. It is thus obviously an error 102, the ultrasound reflectivity of which practically does not depend on that angle, at which the error is impinged upon by the ultrasound beam. Consequently, it is to be assumed that the error, at least with respect to that spatial direction in which the position of the transmitter probe 10 was varied in the above mentioned examination, is largely isotropic.

FIG. 9b, on the other hand, shows an error, the ERS value of which strongly depends on irradiation angle β. This means that the ultrasound reflectivity of error 102 strongly depends on that angle at which the error 102 is captured by the ultrasound beam. At least with respect to that spatial direction in which the transmitter probe was moved for capturing the dependence of the ERS value on the angle, the error 102 that is to be classified is to be seen as being strongly anisotripic. Thus, it can, for example, be a crack that is required to be detected with high probability, and should therefore be graphically emphasized in a suitable way, for example, in a B-scan created by device 1, a C-scan or sector scan, as it was already explained above.

The invention claimed is:

1. A method for nondestructive testing of a test object by means of ultrasound, which comprises the following steps:

a. Radiating directed ultrasonic pulses into the test object at an irradiation angle β, whereby the irradiation angle β is set electronically,
b. recording of echo signals that result from the ultrasonic pulses radiated into the test object,
c. determining an ERS value of an error in the volume of the test object from echo signals that configured to associated with the error by means of a comparison of a majority of the stored reference values and by calculated compensation of the influence of the ERS value of the error that is to be determined by changes in the irradiation angle β, whereby the compensation takes at least one of the following changed sizes into consideration: Change of the virtual ultrasound converter size, change of the position of the injection point, change of the sound path or change of the focus.

2. The method according to claim 1, wherein,
a. for the radiation of directed ultrasound pulses, a transmitter probe is used, the ultrasound transmitter of which comprises a number of independently controllable ultrasound converters, and
b. for the electronic setting of the irradiation angle β, the majority of the ultrasound converters is controlled individually phase-exact in such a way that the angle of radiation α of the ultrasound transmitter is varied.

3. The method according to claim 1, wherein the stored reference values are the following:
c. An AVG diagram of the irradiation angle β, and/or
d. echoes of one or several reference errors measured at the irradiation angle β.

4. The method according to claim 1, wherein the steps of the method a) to c) are performed for at least two different irradiation angles β1, β2, which are electronically set.

5. The method according to claim 1, wherein the majority of stored reference values is correlated with the at least two different irradiation angles β1, β2.

6. The method according to claim 1, wherein, for the automatic compensation of the influence of the electronic adjustment of the irradiation angle β to the determined ERS value of the error, an automatic conversion from radiation angle a of the ultrasound transmitter to the resulting radiation angle β is performed.

7. The method according to claim 1, wherein, for the automatic compensation of the influence of the electronic adjustment of irradiation angle β to the determined ERS value of the error, the variation of the virtual ultrasound transmitter size D' that accompanies the electronic variation of the irradiation angle β, is automatically compensated.

8. The method according to claim 1, wherein, for the automatic compensation of the influence of the electronic adjustment of the irradiation angle β to the determined ERS value of the error, the variation of the position of the focus of the ultrasound beam in the test object that accompanies the electronic variation of the irradiation angle β, is automatically compensated.

9. The method according to claim 1, wherein, for the automatic compensation of the influence of the electronic setting of the irradiation angle β to the determined ERS value of the error, the variation of the position of the injection point X into the test object that accompanies the electronic variation of the irradiation angle β, is automatically compensated.

10. The method according to claim 1, wherein, in an additional step of the method a B-scan, a C-scan, or an S-scan of the test object is shown.

11. The method according to claim 10, wherein at least one of the following display parameters for coding the additional error characteristics that are to be shown is used:
   a. color,
   b. dimension of the bar horizontal to its longitudinal axis,
   c. angle of the longitudinal axis of the bar with respect to the surface of the test object,
   d. geometric basic form of the bar.

12. The method according to claim 1, wherein the illustrated scan an error is symbolized by a bar, and the extension of which along its longitudinal axis is correlated with the ERS value of the error.

13. The method according to claim 12, wherein in the illustrated scan at least one of the following additional characteristics of an error (102 is shown:
   a. relative amplitude of the error echo,
   b. irradiation angle $\beta$, at which the ERS value of the error is at a maximum,
   c. relative error magnitude,
   d. sound path, from which the error echo emanates, and
   e. information about whether the ERS value of the error is essentially constant for different irradiation angles $\beta$.

14. A device for nondestructive testing of a test object by means of ultrasound, with
   a. transmitter probe with an ultrasound transmitter, that is equipped to radiate directed ultrasonic pulses at an irradiation angle $\beta$ into the test object,
   b. an ultrasound receiver, that is equipped to record echo signals that result from the ultrasonic pulses radiated into the test object,
   c. a control and analysis unit, that is equipped,
      i. to control the ultrasound transmitter of transmitter probe in such a way that the ultrasound transmitter is excited to emit ultrasonic pulses,
      ii. to process the echo signals recorded by the ultrasound receiver, and
      iii. to determine an ERS value of error from echo signals that can be associated with an error in the volume of the test object, wherein, that
   d. the ultrasound transmitter comprises a number of independently controllable ultrasound converters, and
   e. the control and analysis unit is equipped:
      i. to control the majority of ultrasound converters individually phase-exact in such a way that the radiation angle $\alpha$ of the ultrasound transmitter and thus the irradiation angle $\beta$ into the test object can be electronically adjusted, and
      ii. to determine the ERS value of an error automatically by comparison with stored reference values,
      iii. to automatically compensate by calculating the influence of the electronic adjustment of the irradiation angle $\beta$ to the ERS value of the error that is to be determined, whereby the compensation takes at least one of the following changes in values into consideration: change of the virtual ultrasound converter size, change of the position of the injection point, change of the focus.

15. The device according to claim 14, wherein the stored reference values are the following:
   a. an AVG diagram of the irradiation angle $\beta$, and/or
   b. echoes of one or more reference errors measured at the irradiation angle $\beta$.

16. The device according to claim 14, wherein
   a. the control and analysis unit is equipped to electronically set at least two different irradiation angles $\beta$, and
   b. the majority of the stored reference values is correlated with the at least two different irradiation angles $\beta$.

17. The device according to claim 14, wherein die control and analysis unit is equipped to automatically compensate the influence of the electronic setting of the irradiation angle $\beta$ to the ERS value of the error that is to be determined, by automatically converting from radiation angle $\alpha$ of the ultrasound transmitter to the resulting irradiation angle $\beta$.

18. The device according to claim 14, wherein die control and analysis unit is equipped for automatic compensation of the influence of the electronic setting of the irradiation angle $\beta$ to the ERS value of the error that is to be determined, by automatically compensating the variation of the virtual ultrasound transmitter size D' that accompanies the electronic variation of the irradiation angle $\beta$.

19. The device according to claim 14, wherein die control and analysis unit is equipped for the automatic compensation of the influence of the electronic setting of the irradiation angle $\beta$ to the determined ERS value of the error, by automatically compensating the variation of the position of the focus of the ultrasound beam into the test object that accompanies the electronic variation of the irradiation angle $\beta$.

20. The device according to claim 14, wherein the control and analysis unit is equipped for automatic compensation of the influence of the electronic setting of the irradiation angle $\beta$ to the determined ERS value of the error, by automatically compensating the variation of the position of the injection point X into the test object that accompanies the electronic setting of the irradiation angle $\beta$.

21. The device according to claim 14, wherein
   a. the probe has a means for capturing position, and
   b. the control and analysis unit is equipped to display a B-scan, a C-scan or an S-scan of test object on the display unit that is associated with device.

22. The device according to claim 21, wherein, in the illustrated scan, an error is symbolized by a bar, the extension of which along its longitudinal axis is correlated with the ERS value of error.

23. The device according to claim 21, wherein, in the illustrated scan, at least one of the following additional characteristics of an error is shown:
   a. relative amplitude of the error echo,
   b. irradiation angle $\beta$, at which the ERS value of the error is at a maximum,
   c. relative error magnitude,
   d. leg, from which the error echo emanates, and
   e. information about whether the ERS value of the error is essentially constant for different irradiation angles $\beta$.

24. The device according to claim 23, wherein at least one of the following display parameters for coding the additional error characteristics that are to be displayed is used:
   a. color,
   b. dimension of the bar horizontal to its longitudinal axis,
   c. angle of the longitudinal axis of the bar with respect to the surface of the test object,
   d. geometric basic form of the bar.

* * * * *